United States Patent [19]

Kauvar et al.

[11] Patent Number: 5,556,942
[45] Date of Patent: * Sep. 17, 1996

[54] GLUTATHIONE S-TRANSFERASE-ACTIVATED COMPOUNDS

[75] Inventors: Lawrence M. Kauvar, San Francisco; Matthew H. Lyttle, Point Reyes Station; Apparao Satyam, Fremont, all of Calif.

[73] Assignee: Terrapin Technologies, Inc., South San Francisco, Calif.

[*] Notice: The term of this patent shall not extend beyond the expiration date of Pat. No. 5,545,621.

[21] Appl. No.: 309,005

[22] Filed: Sep. 19, 1994

Related U.S. Application Data

[63] Continuation-in-part of Ser. No. 130,736, Oct. 1, 1993, which is a continuation-in-part of Ser. No. 126,229, Sep. 24, 1993, which is a continuation-in-part of Ser. No. 863,564, Apr. 3, 1992, abandoned, and a continuation of Ser. No. 253,433, May 31, 1994, said Ser. No. 863,564, is a continuation-in-part of Ser. No. 693,245, Apr. 29, 1991, abandoned, and a continuation of Ser. No. 272,488, Jul. 11, 1994, abandoned.

[51] Int. Cl.$^6$ .......................... A61K 38/06; C07K 5/083
[52] U.S. Cl. ................................ 530/331; 530/345
[58] Field of Search ........................ 514/18; 530/331, 530/345

[56] References Cited

FOREIGN PATENT DOCUMENTS

| | | |
|---|---|---|
| 163550 | 12/1985 | European Pat. Off. . |
| 420121 | 4/1991 | European Pat. Off. . |
| WO90/12088 | 10/1990 | WIPO . |

OTHER PUBLICATIONS

C. Fenselau and P. B. W. Smith, *High–Performance tandem mass spectrometry in metabolism studies*, Xenobiotica, vol. 22, No. 9/10, Sep. 1992–Oct. 1992, pp. 1207–1219.

M. H. Lyttle et al., *Glutathione–S–Transferase Activates Novel Alkylating Agents* Journal of Medical Chemistry, vol. 37, No. 10, 13 May 1994, pp. 1501–1507.

Jane E. Sharer et al., *Formation, stability, and rearrangements of the glutathione conjugates of butadiene monoxide; evidence for the formation of stable surfurane intermediates*, Chem. Res. Toxicol. (1991), 4(4), 430–6 CODEN: CRTOEC; ISSN:0893–228X, 1991, pp. 434–435.

Mannervik, B., et al., Identification of Three Classes of Cytosolic Glutathione Transferase Common to Several Mammalian Species: Correlation Between Structural Data and Enzymatic Properties; *Proc Natl Acad Sci* (1985) 82:7202–7206.

Smith, M. T., et al., Denitrosation of 1,3–Bis(2–chloroethyl)–nitrosourea by Class Mu Glutathione Transferases and Its Role in Cellular Resistance in Rat Brain Tumor Cells; *Cancer Res* (1989) 49:2621–2625.

Castro et al., Differences Among Human Tumor Cell Lines in the Expression of Glutathione Transferases and Other Glutathione–linked Enzymes; *Carcinogenesis* (1990) 11:1569–1596.

Wience, J. K. et al., Human Glutathione S–Transferase Deficiency as a Marker of Susceptibility to Epoxide–Induced Cytogenetic Damage; *Cancer Res* (1990) 50:1585–1590.

Ketterer, B. et al., "Glutathione Conjugation: Mechanisms and Biological Significance" Sies, H., et al. eds. (1988) Academic Press, London, pp. 74–137.

Schisselbauer, J. C., et al., Characterization of Glutathione S–Transferase Expression in Lymphocytes from Chronic Lymphocytic Leukemia Patients; *Cancer Res* (1990) 50:3562–3568.

(List continued on next page.)

*Primary Examiner*—Christine M. Nucker
*Assistant Examiner*—Benet Prickril
*Attorney, Agent, or Firm*—Morrison & Foerster LLP

[57] ABSTRACT

Compounds of the formula:

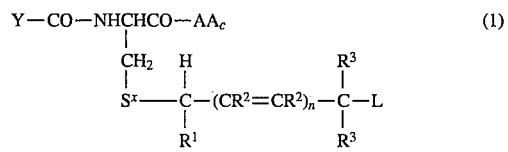

(1)

or the amides, esters or salts thereof, wherein:

L is an electron withdrawing leaving group;

$S^x$ is S=O, O=S=O, S=NH, HN=S=O, Se=O, O=Se=O, Se=NH, HN=Se=O, $S^+R^4$ wherein $R^4$ is alkyl (1–6C), or O—C=O or HN—C=O;

each R of $R^1$, $R^2$ and $R^3$ is independently H or a noninterfering substituent;

n is 0, 1 or 2;

Y is selected from the group consisting of

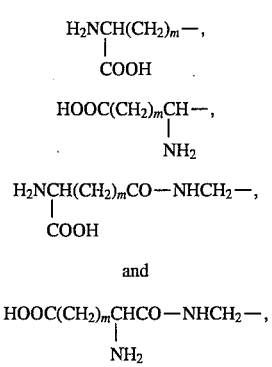

wherein m is 1 or 2; and $AA_C$ is an amino acid linked through a peptide bond to the remainder of said compound of formula 1, are disclosed.

These compounds are useful prodrugs for selective treatment of target tissues which contain compatible glutathione S-transferase (GST) isoenzymes, and simultaneously elevate the levels of GM progenitor cells in bone marrow.

17 Claims, 6 Drawing Sheets

OTHER PUBLICATIONS

Puchalski, R. B., et al., Expression of Recombinant Glutathione S–Transferase π, Ya, or $Yb_1$ Confers Resistance to Alkylating Agents; *Proc Natl Acad Sci USA* (1990) 87:2443–2447.

Borch et al., Synthesis and Antitumor Properties of Activated Cyclophosphamide Analogues; *J Med Chem* (1991) 34:3044–3052.

Borch et al., Synthesis, Activation and Cytotoxicity of Aldophosphamide Analogues; *J Med Chem* (1991) 34:3052–3058.

Borch et al., In Situ Preparation and Fate of cis–4–Hydroxycyclophosphamide and Aldophosphamide; $^1H$ and $^{31}P$ NMR Evidence for Equilibration of cis– and trans–4–Hydroxycyclophosphamide with Aldophosphamide and Its Hydrate in Aqueous Solution; *J Med Chem* (1984) 27:490–494.

Borch et al., The Mechanism of Activation of 4–Hydroxycyclophosphamide; *J Med Chem* (1987) 30:427–431.

Adang, A. E. P. et al., The Glutathione–Binding Site in Glutathione S–Tranferase, Biochem J. (1990) 269:47–54.

Principato, G. B., et al., Effects of Some S–Blocked Glutathione Derivatives on the Prevalent Glyoxalase II (a form) of Rat Liver, Enzyme (1989) 41:175–180.

Morris, D., Synthesis of the a–and y–Isomers of Glutamylcystinylvaline, Biochem J. (1960) 76:349–353.

Waxman, D. J., Glutathione S–Transferase: Role in Alkylating Agent Resistance and Possible Target for Modulation Chemotherapy—A Review; *Cancer Res* (1990) 50:6449–6454.

Mannervik, B. et al., *CRC Crit Rev Biochemistry* (1988) 23:283–355.

Reieneman, P., et al., Three–dimensional Structure of Class π Glutathione S–Transferase from Human Placenta in Complex with S–Hexylglutathione at 2.8 Å Resolution; *J Mol Biol* (1992) 213:214–226.

GLUTATHIONE S-TRANSFERASE-ACTIVATED COMPOUNDS

CROSS REFERENCE TO RELATED APPLICATIONS

This is a continuation-in-part of U.S. Ser. No. 08/130,736 filed 1 Oct. 1993 which is a continuation-in-part of U.S. Ser. No. 08/126,229 filed 24 Sep. 1993, which is a continuation-in-part of U.S. Ser. No. 07/863,564, filed Apr. 3, 1992, and now abandoned in favor of file wrapper continuation 08/253,433 filed 31 May 1994. U.S. Ser. No. 07/863,564 is a continuation-in-part of U.S. Ser. No. 07/693,245, filed Apr. 29, 1991 now abandoned in favor of file wrapper continuation Ser. No. 08/272,488 filed 11 Jul. 1994. The disclosures of these applications are incorporated herein by reference.

TECHNICAL FIELD

The invention relates to glutathione S-transferase-activated compounds. The compounds include glutathione or an analog thereof coupled to a leaving moiety, such as an indicator or a drug moiety, which is released from the glutathione or analog when the compounds are reacted with glutathione S-transferase (GST).

BACKGROUND ART

Glutathione (GSH), in its reduced form, is a tripeptide of the formula: γ-Glu-Cys-Gly. Reduced glutathione has a central role in maintaining the redox condition in cells and is also an essential substrate for glutathione S-transferase (GST). GST exists in mammals as a superfamily of isoenzymes which regulate the metabolism and detoxification of foreign substances introduced into cells. In general, GST can facilitate detoxification of foreign substances by a number of mechanisms and can also convert certain precursors into toxic substances.

GST FUNCTIONS AND STRUCTURE

Waxman, D. J., *Cancer Res* (1990) 50:6449–6454, reviewed the functions performed by GST isoenzymes. As summarized in this report, GSTs can detoxify lipophilic substances which contain an electrophile by catalyzing the coupling of the electrophilic portion to GSH, thus rendering a significant portion of the molecule more polar and susceptible to clearance. A number of the drugs used in cancer chemotherapy are susceptible to this type of detoxification, including, for example, various nitrogen mustards. A second mechanism, which also uses GSH as a substrate, resides in the reduction of peroxides with the concomitant oxidation of GSH; a third simply involves the association of a ligand with the GST in a noncovalent association. Conversely, GSTs also catalyze some reactions which convert nontoxic precursors to toxic agents. For example, GSTs are capable of converting 1,2-dibromoethane and azathiophine to toxins.

As to the catalytic mechanism of GSTs, a review by Mannervik and Danielson (Mannervik, B. et al., *CRC Crit Rev Biochemistry* (1988) 23:283–355) originally suggested the presence of a histidine residue close to the glutathione binding site which would remove the sulfhydryl proton from GSH, generating a nucleophilic sulfide anion. This anion would be more reactive with electrophiles than GSH without the action of GST enzyme. Later crystallographic work with P1 GST (Reieneman, P., et al., *J Mol Biol* (1992) 213:214–226) showed that the actual proton abstracting enzyme moiety was a tyrosine hydroxyl.

PROPERTIES AND DISTRIBUTION OF GST ISOENZYMES

The various GST isoenzymes are dimeric proteins formed by binary combinations of monomers encoded by at least fifteen known genes in four gene families, resulting in the theoretical possibility of several dozen different dimers even allowing for the preferential dimerization of monomers from the same gene family. In addition to the variability that arises from these combinatorial possibilities, the GST isoenzyme subunits are polymorphic in the human population and have been considered to be subject to additional variation due to gene conversion events among the tandemly repeated members of the family. Posttranslational modifications add further to this variability. Thus, the GSTs obtained from tissue samples of a given individual may not necessarily exactly match those of any previously known GST. Particular cell types typically express only a few of these many forms. The particular GST complement in a cell also is probably affected by exposure to certain environmental factors, such as chemical substances, since the enzymes are inducible. GST represents a family of isoenzymes which differ in quantity and enzymatic and physical properties in various cell types and in various individuals.

Mannervik, B., et al., *Proc Natl Acad Sci* (1985) 82:7202–7206, proposed a classification scheme for GST dividing the groups into a single microsomal subclass and three cytosolic subclasses, α, μ and π. These classes show differences in structure, immunological activity, substrate specificity and inhibitor sensitivities.

The ability of different purified rat GST enzymes to detoxify the 1,3-bis-(2-chloroethyl)-1-nitrosourea (BCNU) by denitrosation was studied by Smith, M. T., et al., *Cancer Res* (1989) 49:2621–2625. The reported results indicated that μ isoenzymes containing subunit 4 are the most active catalysts for this reaction while several members of the α subclass had very weak activity.

Thus, each tissue or cell type can be characterized by a particular GST complement—i.e. a set of concentrations of particular GST isoenzymes which is present in the cell or tissue. This is illustrated in Castro et al., *Carcinogenesis* (1990) 11:1569–1596, which describes the results of SDS gel electrophoretic separations of soluble GSTs that had been purified on an S-hexylglutathione Sepharose column. Complements of isoenzymes in various tumor cell lines are compared with purified representatives of the major GST gene families.

ASSOCIATION OF GST ISOENZYMES WITH TUMORS

The association of specific GST isoenzymes with tumors has also been studied. Wiencke, J. K., et al., *Cancer Res* (1990) 50:1585–1590, further describes the art-recognized association of genetic deficiency in the μ isoenzyme of GST with increased lung cancer risk. This deficiency was found to be associated with sensitivity to trans-stilbene oxide-induced cytogenetic damage. Castro et al., 1990, supra, also clearly shows the differences in GST complement, depending on the particular tumor cell line being considered.

The GST π isotype has also been associated with tumors, including cancers of the colon, stomach, pancreas, uterine cervix, renal cortex, adenocarcinoma of the breast and lung, nodular small cell lymphoma, mesothelioma, small cell and nonsmall cell lung carcinoma and EJB bladder carcinoma as well as in CLL (Ketterer, B. et al. in "Glutathione Conjugation: Mechanisms and Biological Significance"; Sies, H., et al. eds. (1988) Academic Press, London, pp. 74–137; Schisselbauer, J. C., et al., *Cancer Res* (1990) 50:3562–3568). It is not considered that the π class of GST is a marker for particular carcinomas or tumors; however antibodies to π GST said to be useful for detecting cancer are disclosed in PCT application WO 90/12088.

The role of the various isoenzymes of GST in conferring resistance to toxins has been confirmed using expression of recombinant GST isoenzymes in mammalian cell transformants; Puchalski, R. B., et al., *Proc Natl Acad Sci USA* (1990) 87:2443–2447. This report showed that each of three full-length cloned GST cDNAs—π (acidic), Ya (basic) and $Yb_1$ (neutral)—conferred drug resistance when expressed in cultured mammalian cells. It was found that GST Ya conferred the greatest increase in resistance to chlorambucil and melphalan; $Yb_1$ conferred the greatest increase in resistance to cisplatin, and π conferred the greatest increase in resistance to racemic benzopyrene mixtures and to doxorubicin. None of these conferred resistance to vinblastine.

The importance of GST in detoxification mechanisms and drug resistance and the availability of a substantial family of isoenzymes which is unevenly distributed as to its members with respect to normal and tumor tissue, combined with differences between the family members in substrate specificity and inhibitor sensitivity, makes this family an important target for designing therapies for conditions associated with malignancy or other unwanted tissue characterized by a discernible GST complement. Methods to obtain GST complements of any particular cell or tissue are outlined in the above-referenced U.S. applications from which priority is claimed.

In particular, it appears that levels of GSTs, especially certain isoenzyme subtypes thereof, are elevated in tumor cells which have acquired resistance to chemotherapeutic drugs. Thus, use of GST-activated prodrugs is particularly effective in targeting tumor cells which have otherwise acquired drug resistance.

Mustards

A particular class of toxic compounds used in chemotherapy, and used for purposes of illustration hereinbelow, are the mustard compounds.

Compounds reported to generate phosphoramide mustards include cyclophosphamide and certain of its analogs (Borch et al., *J Med Chem* (1991) 34:3044–3052) (hereinafter Borch I), as well as aldophosphamide and certain of its analogs (Borch et al., *J Med Chem* (1991) 34:3052–3058) (hereinafter Borch II). Mechanisms of the activation processes that generate phosphoramide mustards from these compounds have been reported (Borch et al., *J Med Chem* (1984) 27:490–494; and Borch et al., *J Med Chem* (1987) 30:427–431.

The release of phosphorodiamidate mustards from perhydrooxazine analogs of aldophosphamide was also reported by Borch et al. (Borch II). Compounds which liberate these "double mustards" were found to exhibit greater cytotoxicity than compounds which liberate phosphoramide mustard (Id.). The increase in observed cytotoxicity is probably due to the ability of the double mustards to crosslink DNA.

Since the mustards produce highly toxic metabolic effects, resulting in deleterious side-effects including death (Borch II), a need exists for compounds which can be designed to target selected cells and predictably release phosphoramide mustards and/or phosphorodiamidate double mustards in the cells that are the intended targets. The prodrugs of the invention are designed for this purpose.

The prodrugs described below may utilize glutathione or its analogs to couple with the drug, rendering the prodrug subject to activation by GST. Some relevant analogs are known in the art.

Adang, A. E. P., et al., *Biochem J* (1990) 269:47–54, described modified forms of GSH in which at least one of the glycine, cysteine, or γ-glutamine residues is replaced by an alternate amino acid residue which interact with various GST isoenzymes at different rates. Additional analogs have been disclosed by Principato, G. B., et al., *Enzyme* (1989) 41:175–180, who studied the effect of a tripeptide GSH analog on glyoxalase II enzyme of rat liver. The tripeptide used by this group was of the formula γ-glu-Cys(p-chlorophenylcarbonylmethyl)-Ser. Morris, D., in *Biochem J* (1960) 76:349–353, described the synthesis of γ-glu-Cys-(benzyl)-Val. GSH tripeptide analogs containing a substitution for only one of the three GSH amino acids have been reported and some are commercially available.

DISCLOSURE OF THE INVENTION

The present invention is directed to GST-activated compounds comprising glutathione (GSH) or an analog thereof coupled to a leaving moiety, such as an indicator or a drug moiety, which is released from the glutathione or analog when the compounds are reacted with GST.

The compounds of the invention are most importantly prodrugs, for instance for a cytotoxic drug intended to destroy tumor cells. These prodrugs may be substrates only for selected GST isoenzymes, and are capable, for example, of selectively killing cells with particular complements of GST isoenzymes where at least one isoenzyme of GST is elevated or with elevated GST levels in general. This is particularly important in the design of chemotherapeutic treatment since drug resistance by tumor cells is often characterized by elevated levels of one or more GSTs. Thus, the very cells which are most refractory to conventional treatment are the most susceptible to attack by the cytotoxic agents included in the prodrugs of the invention. The elevated levels of GST present in these cells enables them to facilitate the release of the cytotoxic agent intracellularly in the tumor, as compared to the capability of normal cells. In one illustration the present invention provides glutathione or an analog coupled to cytotoxic phosphorodiamidate mustard moieties. When reacted with GST, the prodrugs will liberate the phosphorodiamidate mustard. This provides a method for delivering this cytotoxic agent only to selected tissue or cells, such as tumor cells.

The compounds of the invention have also been shown to stimulate the production of granulocyte macrophage (GM) progenitors in bone marrow of animals to which the compounds are administered. It is unclear whether the prodrug-type compound itself or its metabolic products are responsible for this effect.

Alternatively, the leaving moiety of a compound of the invention may comprise an indicator, which when released from a compound of the invention can be readily detected and conveniently used to monitor the extent of such cleavage reaction, e.g., colorimetrically. A compound of the invention comprising an indicator moiety, such as p-nitrophenol which is colorless when coupled in the prodrug but develops a color on release by GST, is a useful reagent in a method of assaying GST activity. This includes GST isoenzyme-specific assays using reagents comprising certain GSH analogs that are substrates only for selected GST isoenzymes.

Accordingly, in one aspect, the invention is directed to a compound of the formula:

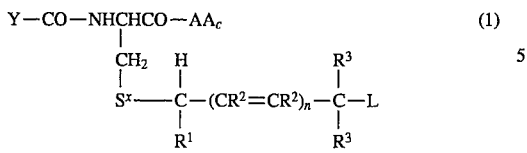

or the amides, esters or salts thereof, wherein:

L is an electron withdrawing leaving group;

$S^x$ is $S=O$, $O=S=O$, $S=NH$, $HN=S=O$, $Se=O$, $O=Se=O$, $Se=NH$, $HN=Se=O$, $S^+R^4$ wherein $R^4$ is alkyl (1-6C) or $O-C=O$ or $HN-C=O$;

each R of $R^1$, $R^2$ and $R^3$ is independently H or a noninterfering substituent;

n is 0, 1 or 2,

Y is selected from the group consisting of

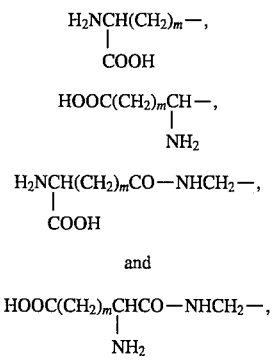

wherein m is 1 or 2; and $AA_C$ is an amino acid linked through a peptide bond to the remainder of said compound of formula 1.

In other aspects, the invention is directed to methods of synthesizing the compounds of formula 1, to pharmaceutical compositions containing these compounds, and to methods to treat tumor cells by administering the compounds of formula 1 in context where the prodrugs are selectively cleaved by the tumor cells to release the cytotoxic agent.

In still other aspects, the invention is directed to methods of providing chemotherapeutic agents while protecting the function of bone marrow in vertebrate subjects by administering the prodrugs of the invention and to methods selectively to treat tumor cells with characterized GST contents by selectively administering the prodrugs of the invention that are sensitive to cleavage with a GST that shows an elevated level in the target cells.

MODES OF CARRYING OUT THE INVENTION

Figure 1:
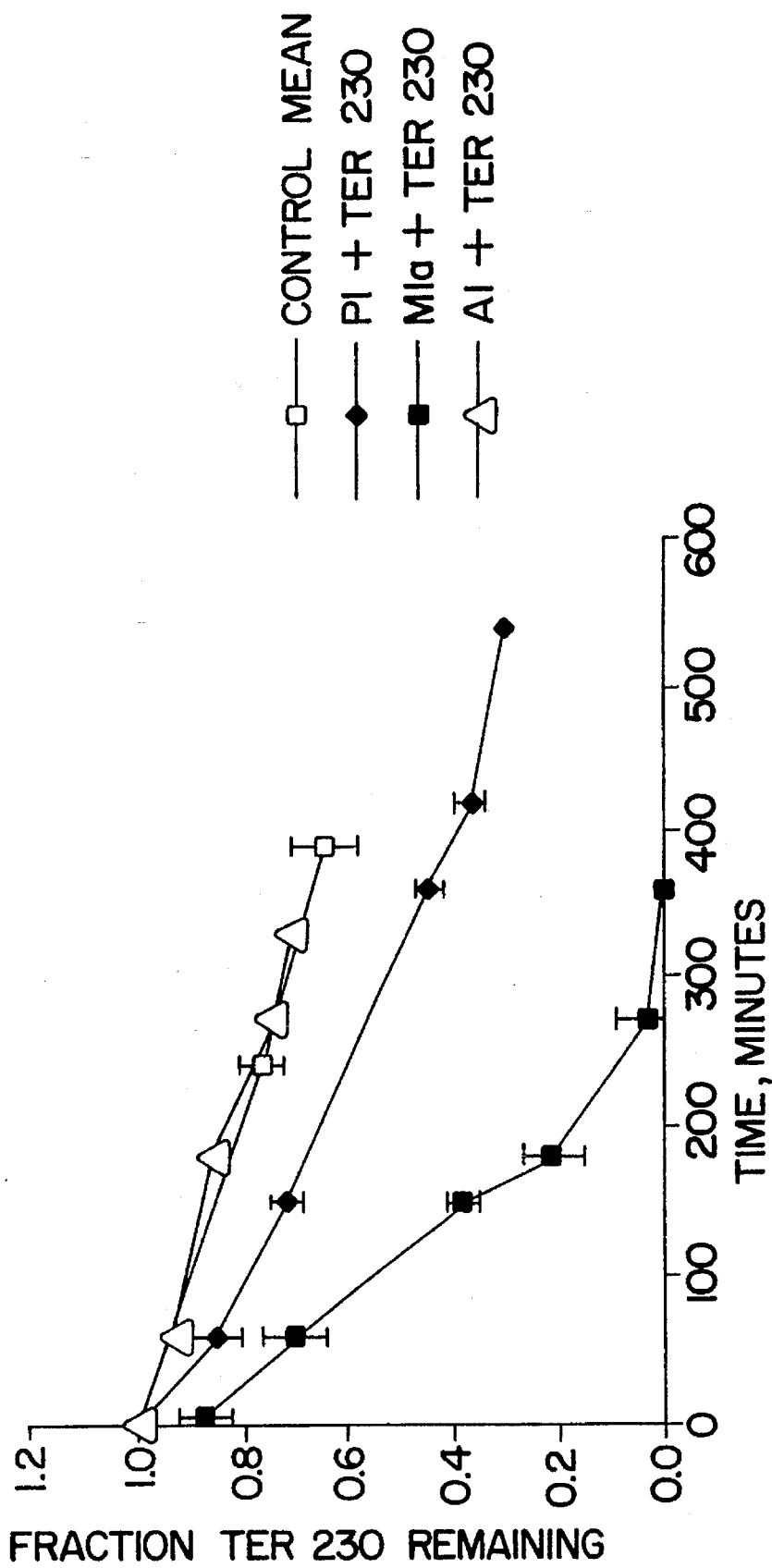
FIG. 1 is a graph showing the decomposition of TER 230 by various GSTs.

The compounds of formula 1 are prodrugs which can be used selectively to target tissues having GST complements which are elevated or which are peculiar in specificity to the prodrug provided. As shown below, the prodrugs prepared for illustration, TER 230, as a model compound, and TER 231, TER 286, TER 296 and TER 303 as effective prodrugs, are differentially activated by GST enzymes of the μ, π and α classes. These prodrugs, in addition to being selective for cells with elevated GST complements per se, can be used in a finely tuned protocol to target cells which have elevated levels of a particular isoenzyme of the GST group.

The prodrugs of the invention have an additional advantage—they are protective of bone marrow and thus permit higher or more intensive dosages to be used. Thus, not only is the chemotherapeutic effect of the released cytotoxic agent focused on the target cells, the compounds of the invention are able to potentiate the function of bone marrow as measured by the ability of these compounds to stimulate the production of GM progenitor cells by bone marrow, thus enhancing protection of normal tissue. The mechanism of this potentiation, manifested by an increase in the production of granulocyte macrophages, is unclear. This potentiation may be useful in the treatment of anemia. It is at present also unclear whether the prodrug itself or its metabolic products, for example, the glutathione analog which is generated by cleavage of the parent compound, is responsible for this effect.

In an additional use, the compounds of formula 1 can be used as analytical reagents for GST activity by employing as "L" an indicator group which is detectable when liberated from the compound of formula 1. Such a reagent is suitable for determining the concentration of GST of known substrate specificity, or analyzing the specificity of particular GSTs by varying the glutathione analog component of the compound of formula 1.

COMPOUNDS OF THE INVENTION

The compounds of the invention of formula 1 are comprised of a tripeptide which is glutathione or an analog thereof coupled to a leaving group through a molecular system which permits release of the leaving group L when the compound of formula 1 is treated with the appropriate GST. The release of the leaving group occurs through a "β-elimination"—i.e., the removal of the proton on the carbon α to the electron-poor carbon, sulfur or selenium releases electrons which are ultimately absorbed by the leaving group and result in its release. This can be shown schematically as follows:

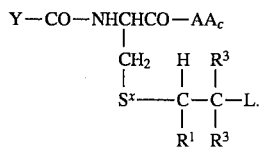

The electron pair can be released to the leaving group directly through β-elimination as shown above or through a system of conjugation represented by $(CR^2=CR^2)_n$ in formula 1. Thus, n may be 0, 1 or 2; theoretically n can be any integer but the efficacy of the electron transport is believed to decline as n increases.

The substituents $R^1$, $R^2$ and $R^3$ play no direct part in the release of substituent L and simply must be noninterfering substituents. The rate of β-elimination can be controlled by the nature of these R groups; by choosing electron withdrawing or electron donating substituents the rate of elimination can be accelerated or decreased. Suitable substituents for $R^1$ and $R^3$ include H, substituted or unsubstituted alkyl (1–6C) substituted or unsubstituted aryl (6–12C), substituted or unsubstituted aryl alkyl (7–12C), cyano, halo, substituted or unsubstituted alkoxy (1–6C), substituted or unsubstituted aryloxy (6–12C) or substituted or unsubstituted arylalkyloxy (7–12C).

Alkyl, aryl, and arylalkyl have their conventional meanings; alkyl groups are straight, branched chain or cyclic saturated hydrocarbon moieties such as methyl, tert-butyl, cyclohexyl, and the like. Aryl groups include aromatic systems such as phenyl, naphthyl, pyridyl and the like. Arylalkyl substituents contain an aryl moiety coupled to the remainder of the molecule through an alkylene moiety. Such groups include, most commonly benzyl, phenylethyl, 2-pyridylethyl, and the like.

Suitable substituents in the substituted forms include halo, SR, OR, and $NR_2$ wherein R is H or lower alkyl (1–4C).

Preferred embodiments for $R^1$ and $R^3$ independently are H, lower alkyl (1–4C) and phenyl. $R^2$ may preferably be H or alkyl (1–6C). In particularly preferred embodiments, $R^1$ is H or phenyl, both $R^3$ are H and n=0. However, any noninterfering substituents may be used as $R^1$, $R^2$ and $R^3$. These substituents are independently embodied.

The embodiments of Y—CO and —$AA_C$ determine the nature of the glutathione-like tripeptide. A preferred embodiment is that wherein Y—CO is γ-glutamic and $AA_C$ is glycine, phenylglycine, β-alanine, alanine or phenylalanine, resulting in the tripeptide glutathione or a close analog. However, alternative embodiments of Y—CO include β-Asp, Glu, Asp, β-GluGly, β-AspGly, GluGly and AspGly. Alternative embodiments of $AA_C$ include, along with the preferred glycine, phenylglycine, β-alanine, alanine, and unsubstituted phenylalanine: valine, 4-aminobutyric acid, aspartic, phenylglycine, histidine, tryptophan, tyrosine, and substituted phenylalanine. Suitable phenylalanine substituents are as described above for the substituted forms of $R^1$ through $R^3$.

Suitable embodiments for L include those which generate drugs which may be cytotoxic to unwanted cells. Such drugs include the phosphoramide mustards, the phosphorodiamidate mustards, the chemotherapeutic agents adriamycin and daunorubicin, toxins such as ricin toxin or diphtheria toxin, antiinflammatory or steroid-based drugs and the like, and other metabolic modulators such as 2,3-di-t-butyl- 4-hydroxyanisole. Preferred forms of the phosphorodiamidate mustards are —OP(O)(N(CH$_2$CH$_2$Cl)$_2$)$_2$, —OP(O)(N(CH$_2$CH$_2$Br)$_2$)$_2$, —OP(O)(NHCH$_2$CH$_2$Cl)$_2$ and —OP(O)(NHCH$_2$CH$_2$Br)$_2$. Any biologically active moiety, provided with an electron adsorbing linkage to the remainder of the compound so that "L" released by β-elimination may be used.

In addition, indicator molecules such as p-nitrophenol can be used when the compound of formula 1 is intended as a reagent.

Particularly preferred compounds of the invention are:

γ-glutamyl-α-Amino-β-((2-ethyl-N,N,N,N-tetra(2'-chloro-)ethylphosphoroamidate)sulfonyl)propionylglycine, (TER 231);

γ-glutamyl-α-Amino-β-((2-ethyl-N,N,N,N-tetra(2'-chloro-)ethylphosphoroamidate)sulfonyl)propionyl-(R)-(–)phenylglycine (TER 286);

γ-glutamyl-α-Amino-β-((2-ethyl-N,N,N,N-tetra(2'-chloro)ethylphosphoroamidate)sulfonyl)propionyl phenylalanine (TER 303);

γ-glutamyl-α-Amino-β-(1-phenyl, 2-ethyl-N,N,N,N-tetra(2'-chloro)ethylphosphoroamidate)sulfonyl)propionyl glycine (TER 296);

γ-glutamyl-α-Amino-β-(1-phenyl, 2-ethyl-N,N,N,N-tetra(2'-chloro)ethylphosphoroamidate)sulfonyl)propionyl (R)-(–)-phenylglycine (TER 297).

The compounds of the invention may also be prepared in the forms of their esters or amides, or as their salts. The esters, amides or salts are formed with any or all carboxyl groups present in the molecule; hence, included in this group are monoesters, diesters, and, if applicable, triesters. Similarly, monoamides, diamides, or, if applicable, triamides are included.

The esters or amides may be alkyl (1–6C), alkenyl (1–6C) or arylalkyl (7–12C). Alkyl esters of the free carboxyls are esters of the straight- and branched-chain alkyl alcohols (1–6C) such as methanol, ethanol, isopropanol, t-butanol, n-hexanol and the like. Suitable alkyl (1–6C) amides are those of primary straight- or branched-chain alkyl amines, such as methylamine, ethylamine, n-propylamine, isopentylamine, and isohexylamine. Alkenyl esters are similar, but contain at least one double bond. Arylalkyl is as defined above. The alcohols or amines may also carry noninterfering substituents such as halo, alkoxy, or alkyl amines. The esters and amides are prepared using conventional techniques, with suitable protection of any alcohol or amino functional groups in the compound of formula 1.

The salts of the compounds of the invention may be formed of inorganic or organic bases to form the basic salts of the free carboxyl groups or may be formed from organic or inorganic acids to obtain the acid addition salts of free amino groups. Thus, the salts may be of inorganic bases such as sodium hydroxide, potassium hydroxide, calcium hydroxide, ammonium hydroxide, magnesium hydroxide, and the like, or of organic bases such as trimethylamine, pyridine, pyrimidine, piperidine, lysine, caffeine, and the like. The acid addition salts may be formed from inorganic acids such as hydrochloric acid, hydrobromic acid, sulfuric acid, phosphoric acid, and the like, or from organic acids such as acetic acid, propionic acid, glycolic acid, pyruvic acid, oxalic acid, malic acid, tartaric acid, citric acid, benzoic acid, cinnamic acid, mandelic acid, salicylic acid, and the like. Salts of citric acid are preferred.

The salts of the compounds of formula 1 are formed in standard protocols by treating with the appropriate base or acid at a temperature of from about 0° C. to about 100° C., preferably at room temperature either in water alone or in combination with an inert water-miscible organic solvent such as methanol, ethanol or dioxane.

Use of the Invention Compounds for Targeted Drug Delivery

The invention provides a general vehicle for delivering drugs to tissues specifically based on their GST content. The leaving group, when released in the target tissue, will exert its desired effects selectively in that target tissue. In addition to cytotoxicity, the released moiety may have other regulatory features. For example, where "L" is 2,3-di-t,butyl-4-hydroxyanisole, this compound is known to induce the synthesis of GSTs in mice. Administration of the compound of formula 1 wherein "L" will release this moiety may result in concomitant increase in GSTs. The target cells where release will occur can be regulated by manipulating the nature of the glutathione analog portion of the molecule. It may be desirable to enhance the GST component of the tumor cells concomitantly with supplying a compound of formula 1 containing a cytotoxin.

As described above and demonstrated in the examples below, the various prodrugs of the invention are selective for the various isozymes of GST whose levels may be elevated in tumor cells. By determining the profile of GST isoenzyme levels in the tumor target, and matching this with the specificity of the prodrug, maximum effectiveness against the tumor cell will be obtained and maximum selectivity for the tumor cell as opposed to normal tissue can be achieved. As shown below, the selectivity of the prodrug depends on the choice of the glutathione analog used as a component of the drug. In the compounds exemplified below, TER 231 is especially susceptible to cleavage by GST M1a-1a; TER 303 is especially susceptible to cleavage by A1-1; TER 286 is particularly susceptible to cleavage by P1-1 and A1-1, while TER 296 is selectively cleaved by P1-1. Thus, in treating a tumor having elevated levels of P1-1, use of TER 296 would be preferred. The prodrugs of the invention are particularly favored for treatment of subjects since in addition to cytotoxicity to the tumor, they appear to stimulate GM progenitors in bone marrow. There is relatively little organ toxicity and no evidence of leukocytosis. For TER 286, the relevant isoenzyme, GST P1-1 is elevated in more than 75% of human tumor specimens from breast, lung, liver and colon.

The compounds of formula 1 are administered as pharmaceutical compositions in usual formulations such as those outlined in *Remington's Pharmaceutical Sciences*, Mack Publishing Company, Easton, Pa., latest edition. Typical formulations will include those for injection, for transdermal and transmucosal administration, and for oral administration. The formulations, depending on the intended mode, may be liquids, syrups, powders, capsules, suppositories, and the like. The compounds of the invention may be included in liposomes, or in other emulsified forms. Protocols for administration and suitable formulations are subject to optimization using standard procedures known to those in the art.

The antitumor activity of the invention compounds coupled with phosphorodiamidate mustard or other toxins can be assessed using a number of human tumor xenographs to determine tumor growth inhibition or a B16 mouse melanoma and measuring the prolongation of survival to determine the efficacy of particular compounds.

Compounds for Assay of GST Isoenzyme Activity

An alternative use for the compound of formula 1 is as a reagent in assays where the moiety "L", when released from the compound can be readily detected. The compounds of formula 1 can thus conveniently be used to monitor the extent of the GST cleavage reaction, e.g., colorimetrically. Thus, an indicator moiety, such as p-nitrophenol, which is colorless when coupled to GSH or a GSH analog but develops a color on release from the compound by GST, offers an improved method of assaying GST activity. GST isoenzyme-specific assays using compounds comprising certain GSH analogs that are substrates only for selected GST isoenzymes can be used to determine substrate specificity.

Synthesis of the Invention Compound

The compounds comprising glutathione or its analogs described above coupled to a desirable leaving group can be synthesized using means generally known in the art. Where $S^x$ is an oxidized form of S or Se, the methods illustrated below can be used, incorporating modifications which render them applicable to desired compounds of the invention. In general, the compounds of formulas 2, 11 and 12 can serve as intermediate compounds in the synthesis of compounds of formula 1.

Thus, for example, compounds of formula 1 wherein $S^x$ is S=O, Se=O, O=S=O or O=Se=O can be produced from the corresponding compounds of formula 2 wherein $S^\tau$ is S or Se, respectively, by oxidation with mild oxidizing agents such as peroxide or peracetate. Compounds of formula 1 wherein $S^x$ is S=NH, Se=NH, O=S=NH, or O=Se=NH can be obtained by treatment of the appropriate precursor of formula 2, or a partially oxidized form, with chloramine T under conditions known in the art. Alternatively, the method of Whitehead, J. K. et al., *J Chem Soc* (1952) 1572–1574, may be used. Compounds of formula 11 or formula 12 can be converted to the compound of formula 1 by coupling the Y—CO moiety through a peptide linkage to the compound of formula 12 or the $AA_C$ amino acid to the compound of formula 11 using standard peptide coupling techniques. When S* is S or Se in reduced form in the compounds of formulas 11 and 12, these compounds may, similarly, be converted to compounds of formula 2. Compounds of formula 1 wherein $S^x$ is a sulfonium ion, i.e., is $S^+$; may be synthesized by treating compounds of formula 2 with alkyl halides under suitable conditions to alkylate the sulfide, or intermediates can be synthesized from corresponding compounds of formula 11 or 12. $R^4$ is alkyl (1–6C) as defined above. Preferred alkyl halides for reaction to form, ultimately, compounds of formula 1 in this embodiment are the iodides.

For compounds of formula 1 wherein $S^x$ is O—C=O are obtained using as a dipeptide or tripeptide starting material analogs of glutathione wherein serine substitutes for the cysteine moiety. Compounds of the formulas 11, 12 and 1 are then obtained by esterification of the di- or tripeptide containing serine. Where $S^x$ is NH-C=O, the corresponding amidation reaction is effected with analogs wherein 2,3-diaminopropionic acid replaces cysteine.

Two preferred methods of synthesis are illustrated below. The synthesis of TER 230, a model compound, is used to illustrate Reaction Scheme 1.

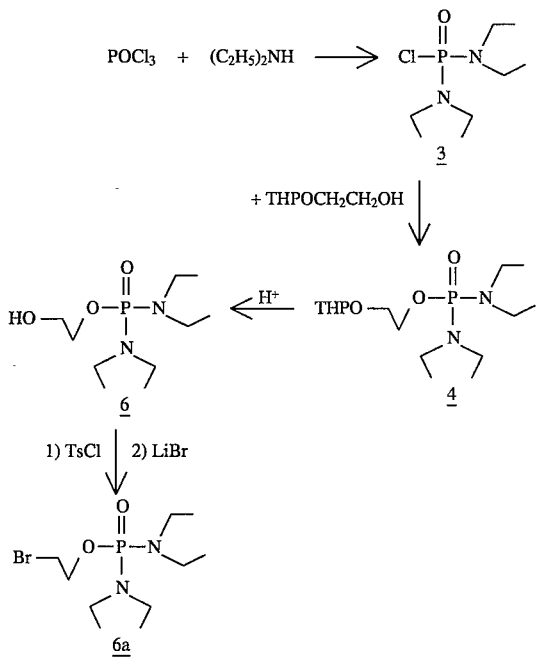

-continued
Reaction Scheme 1

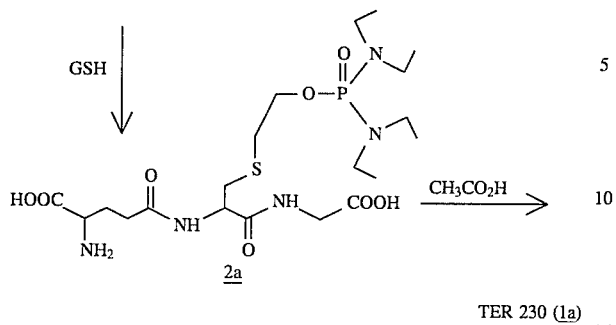

TER 230 (1a)

TER 230 is thus made by alkylating GSH with 2-bromoethyl-N,N,N,N,-tetraethyl phosphorodiamidite. Two equivalents of diethylamine are added to phosphorus oxychloride to give compound 3, following the procedure of Borch, et al., *J Med Chem* (1991) 34:3052–3058. 3 is then alkylated with monotetrahydropyranyl ethylene glycol (prepared as described by Satyam, A. and Narang, S. *Polymer Reprints* (1992) 33:122–123, to give compound 4 which is hydrolyzed with acid to remove the THP protecting group and then converted into the bromide 6a in two steps by conversion to the tosylate, followed by reaction with lithium bromide to give 6a. 6a is then added to glutathione to give the sulfide 2a, which is oxidized with peracetic acid to give TER 230, 1a.

Reaction Scheme 2 summarizes the manner in which the synthesis of TER 231 is exemplified below. TER 231 is a prodrug of the invention which, when activated with GST, releases a cytotoxic mustard.

Reaction Scheme 2

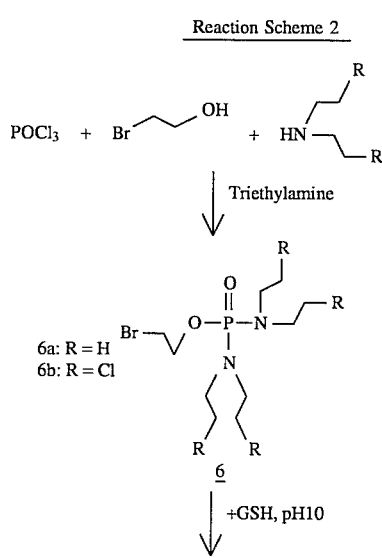

-continued
Reaction Scheme 2

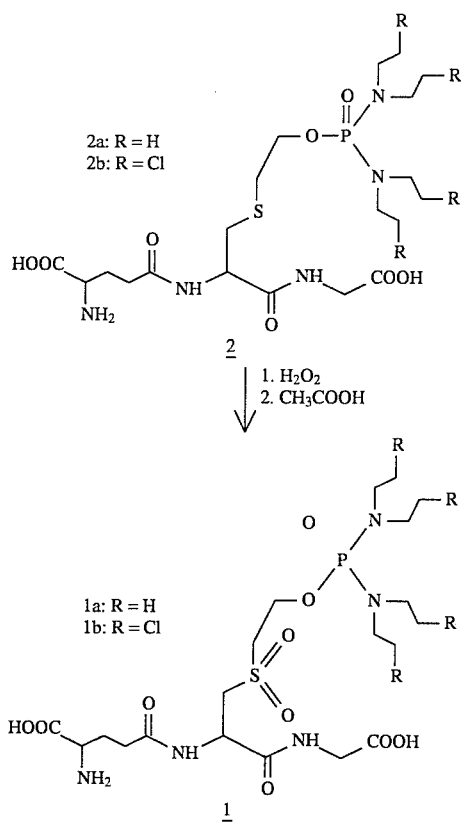

As shown in Reaction Scheme 2, the crucial intermediate 6b, for example, is synthesized in a simplified manner by the reaction of phosphorous oxychloride with 2-bromoethyl alcohol and bis-(2-chloroethyl) amine hydrochloride. Appropriate conditions for this reaction are described in Example 2 below. The remaining steps in the synthesis are analogous to those in Reaction Scheme 1.

In a preferred embodiment illustrated in both reaction schemes, the coupled compound of formula 1 is first synthesized as a reduced form of formula 2 to prevent elimination of phosphate. The compound of formula 2 is thus oxidized in the final step of the synthetic process to prevent decomposition of the molecule.

While the examples below provide experimental details for the synthesis of TER 230 and TER 231, this general reaction scheme is applicable to the compounds of the invention in general substituting the appropriate components for intermediate 6 which provides the leaving group and the appropriate tripeptide acceptor containing a cysteine moiety. Appropriate modifications of GSH shown in Reaction Scheme 2 results in the desired prodrug. For example, for synthesis of TER 296 or TER 297, α-amino-β-sulfhydryl-β-phenylpropionic acid is substituted for the cysteine residue in the analog. For the synthesis of TER 286, phenylglycine is substituted for glycine in the tripeptide as $AA_c$. For synthesis of TER 303, phenyl alanine is substituted for glycine as $AA_C$ in the GSH analog.

At least one proton positioned alpha to the electron-deprived atom of $S^x$ and effectively beta to the phosphate oxygen must be sufficiently acidic to be removed by the basic moiety believed to reside in the GST active site to allow release of the phosphorodiamidate mustard. The electron withdrawing or donating nature of $R^1$ can be used to regulate the rate of reaction by affecting the acidity of this proton. The nature of $R^3$ is also significant. For example an embodiment wherein both $R^3$ are methyl lowers the energy of the transition state for the enzyme-catalyzed β-elimination.

The following examples are intended to illustrate, but not to limit, the invention.

EXAMPLE 1

Synthesis of Glutathione Coupled to Phosphorodiamidate:
γ-glutamyl-α-aminopropionyl (β-(2-ethyl-N,N,N,N,tetraethylphosphoramidate) sulfonyl)-glycine (TER 230)

This example describes the synthesis of TER 230, of the formula:

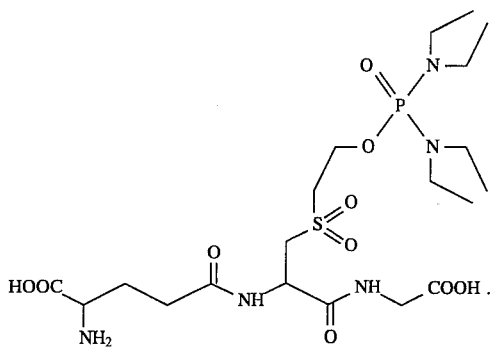

When used as a model compound and contacted with GST, TER 230 undergoes β-elimination to give

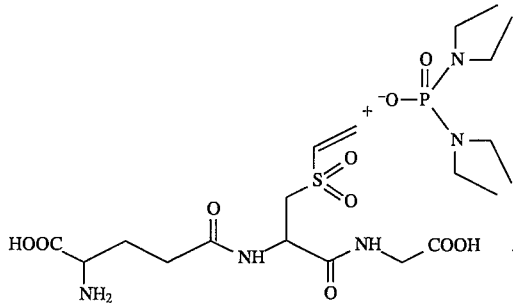

The synthesis of this compound is summarized in Reaction Scheme 1.

Chloro-N,N,N,N-tetraethyl phosphordiamidate, 3

Diethylamine (33.72 ml, 360 mM) was added dropwise with stirring to a cooled (0°–5° C.) solution of phosphorus oxychloride (15.2 ml, 160 mM) in 1 L $CH_2Cl_2$ to which triethylamine (50 ml, 360 mM) had been previously added dropwise. The solution was allowed to warm to rt. and stirred for three days. The reaction was quenched by cooling to 0° and adding 10% $KH_2PO_4$ in water, 200 ml. The mixture was warmed to room temperature. The mixture was poured into a sep. funnel, and separated. The lower organic layer was saved, and the aqueous layer was extracted with 100 ml of $CH_2CL_2$. The combined organic phases were washed with 500 ml saturated brine and dried over $Na_2SO_4$. The solution was filtered and reduced to an oil under vacuum. Some solid material was removed from the oil by additional filtration. TLC analysis (EM #5534 F 254, developed with hexane:EtOAc 1:1 and visualized with iodine vapor) showed that two products were present, the major product, rf 0.3, was isolated by column chromatography using JT Baker FC silica, 40 m eluted isocratically with hexane:EtOAc 4:1. Column fractions containing the pure lower rf compound were pooled and evaporated to give 12 g (33% yield) of a pale yellow oil. $^1$H NMR, $CDCl_3$, PPM: 3.3–3.05, q, j=5.3 Hz. 1.2–1.05, t, j=5.3 Hz. M/e (rel. intens.) 227.1 (100,MH+), 191.2 (11), 154.1 (38), 136.1 (28).

Monotetrahydropyranyl ethylene glycol

Dihydropyran (18.25 ml, 200 mM) was added dropwise to a cold (0°) mixture of ethylene glycol (55.92 ml, 1 mol) in 500 ml $CH_2Cl_2$ containing 3.8 g (20 mM) of dissolved p-toluene sulfonic acid monohydrate over 2 hrs. The mixture was allowed to stir for an additional 2 hrs at this temperature, and then was allowed to warm to rt. Stirring continued for 2 days, after which the mixture was poured into a separating funnel and allowed to separate. The lower organic layer was removed and saved, and the upper layer was extracted with 100 ml $CH_2Cl_2$. The combined $CH_2Cl_2$ layers were washed six times with 100 ml portions of saturated NaCl, and dried over $Na_2SO_4$. The solution was filtered and reduced, and the residue was purified by chromatography with the same silica as above. The column was eluted isocratically with 3:2 EtOAc:hexane which contained 1% triethylamine (TEA). Fractions which contained pure product, rf 0.5 (using the same TLC system as above) were pooled and evaporated to give 9.7 g (33% yield) of a colorless oil. $^1$H NMR (300 mHz, $CDCl_3$, PPM) 5.6–5.5, m, 1H. 4.0–3.9, m, 1H. 4.8–4.65, m, 4H. 3.6–3.5, m, 1H. 1.9–1.7, m, 2H. 1.65–1.5, m, 4H.

2-Tetrahydropyranyloxyethyl-N,N,N,N-tetraethylphosphorodiamidate, 4

A solution of 4.4 g (30 mM) monotetrahydropyranylethylene glycol prepared above in 25 ml of THF which had been freshly collected from a sodium benzophenone THF still under argon was added dropwise to a stirred solution at 0° of 0.72 g (30 mM) sodium hydride in 50 ml of the same dry THF. To this was added a solution of 5.67 g (25 mM) 2 in 25 ml THF over 10 min, and this was stirred for 18 hrs at rt. TLC (same system as above, except eluted with EtOAc:MeOH 9:1. The reaction was quenched with dropwise addition of 100 ml water, and extracted twice with 250 ml portions of EtOAc. The combined organic extracts were washed twice with 100 ml portions of brine and dried over $Na_2SO_4$. This was filtered and evaporated to 8.3 g (98% yield) of an oil which was used without further purification. $^1$H NMR (300 mHz, $CDCl_3$, PPM) 4.65, m, 1H. 4.1–4.0, m, 1H. 3.9–3.8, m, 1H. 3.7–3.6, q (j=5.6 Hz), 1H. 3.55–3.45, m, 1H. 3.1–3.0, dq (j=4.35, 16.3 Hz), 8H. 1.85–1.5, M, 6H. 1.15–1.05 t (j=16.3 Hz), 12 H. M/e (Rel. Intens.) 337.2, (MH+, 28), 253.1 (100), 235.1(12), 80.1 (22).

2-Hydroxyethyl-N,N,N,N-tetraethylphosphorodiamidate 8.3 g (24.7 mM) of 2-Tetrahydropyranyloxyethyl-N,N,N, N-tetraethylphosphorodiamidate prepared above was dissolved in 200 ml of methanol and a 190 mg p-toluene sulfonic acid was added. The mixture was heated to reflux for 8 hr, cooled, and 3 ml of TEA was added. The material was reduced and purified by chromatography, using 36 g of the same silica as above, eluted with EtOAC. Fractions containing product (rf 0.5, EtOAc:MeOH 9:1) were pooled and evaporated to give 4.5 g (72% yield) of colorless oil. $^1$H NMR (300 mHz, $CDCl_3$, PPM) 4.1–4.0, dt (j=12.7, 2.3), 1H.

3.8, t (j=2.3), 1H. 3.7–3.6, broad s, 1H (disappears with D$_2$O). 3.2–3.0, symmetrical 11 peak resonance, j=3.4 Hz, 8H, 1.2–1.1, t (j=7.0), 12 H. M/e (Rel. Intens.) 253.1 (MH+, 100), 180.1 (11).

2-p-Toluenesulfonyloxyethyl-N,N,N,N-tetraethylphosphorodiamidate

A solution of 4.5 g (23 Mm) p-toluene sulfonylchloride in 10 ml THF was added dropwise to a stirred solution of 4.5 g (17.9 mM) 2-Hydroxyethyl-N,N,N,N-tetraethylphosphorodiamidate prepared above and 1.6 g (40 mM) NaOH in 12 ml THF and 8 Ml water at 0° over a period of 2 hrs. The mixture was allowed to warm to rt and stirred overnight. The mixture was poured into 35 ml of water and extracted with two 50 ml portions of toluene, and the combined organic phases were dried over Na$_2$SO$_4$ and concentrated to a viscous oil. TLC (9:1 EtOAc:MeOH) showed one spot, rf 0.7, UV active. The yield was 7.32 g, 99%. $^1$H NMR (300mHz, CDCl$_3$, PPM) 7.8, d (j=8.3), 2H. 7.35, d (j=8.3), 2H. 4.2, m, 4.1–4.0, m, 2H. 3.1–2.9, m, 8H. 2.45, s, 3H. 1.15–1.0, t (j=7.1), 12 H. M/e (Rel. Intens.) 407.1 (MH+, 100), 334.0 (24), 253.1 (49), 199.0 (20).

2-Bromoethyl-N,N,N,N-tetraethylphosphorodiamidate, 6a 7.2 g (17.8 mM) of the tosylate above was dissolved in 125 ml acetone and 3.04 g (35 mM) of LiBr was added. The mixture was refluxed for 7 hrs, cooled, and allowed to stand 2 days. The mixture was filtered and the residual solids washed with 25 ml acetone. The filtrate and washes were stripped to a gummy solid. This material was triturated with 100 ml CH$_2$Cl$_2$, filtered, and the liquid reduced to an oil. $^1$H NMR (400 mHz, CDCl$_3$, PPM) 4.25, m, 2H. 3.6, m, 2H. 3.1–3.0, m, 8H. 1.05, t (j=7 Hz), 12H. M/e (Rel. Intens.) 323.1 (96), 321.1 (100, MH+with 1 bromine), 241.2 (26), 191.2 (14).

γ-Glutamyl-α-aminopropionyl β-(2-ethyl-N,N,N,N,-tetraethylphosphoramidate)-sulfidyl-glycine, 2a 250 mg (0.8 mM) glutathione was dissolved in 5 ml of water and brought to pH 12 with conc. NaOH solution. This was added, with stirring, to a solution of 300 mg (0.95 mM) 6a in 5 ml ethanol. The reaction was stirred 4 hrs and neutralized with 1N HCl. A clear product, TLC spot rf 0.66 (1:1:1:1 butanol:HOAc:EtOAc:water), visualized with ninhydrin spray, was present. The solution was concentrated to a solid and purified by HPLC: A 141 column packed with 5 m C-18 functionalized silica (YMC Corp.) was flushed with 90% CH$_3$CN in 0.2% HOAc (B) water followed by equilibration with 300 ml of 0.2% HOAc (A) at 12 ml/min flow rate. The crude sulfide was dissolved in 20 ml of water and loaded onto the column, followed by 100 ml of A. A gradient to 50% B was run over 90 min, and fractions which appeared clean by TLC were pooled and lyophilized. The yield was 240 mg (55%) of white powder, over 90% pure by analytical HPLC, mp 100°–105° C. $^1$H NMR (400 mHz, CDCl$_3$, PPM) 4.3, m, 1 H. 3.8, m, 2H, 3.7, s, 2H. 3.5, m, 1H., 2.9–2.5, m, 12 H. 2.2, m, 2H. 1.9, m, 2H. 0.8, t (j=7 Hz), 12H. M/e (Rel. Intens.) 564.2 (M+Na, 18). 542.2 (MH+, 100). 306.1 (32). 209.2 (26). 177.1 (43).

Anal. Calc'd for C$_{20}$H$_{40}$N$_5$O$_8$PS.HOAc-½HCl: C, 42.63. H, 7.23. N, 11.29. Found: C, 42.18. H, 6.58. N, 11.51.

γ-glutamyl-α-aminopropionyl(β-(2-ethyl-N,N,N,N,-tetraethylphosphoramidate)-sulfonyl)-glycine (TER 230)

528 mg (0.97 mM) 2a was dissolved in 10 ml HOAc with sonication, and 400 ml (2 mM) of 30% H$_2$O$_2$ was added. The mixture was stirred at rt for 2½ hr, and 200 ml of 32% peracetic acid was added. The mixture was stirred for 3 days, and was quenched with 200 ml of dimethyl sulfide. The material was lyophilized to a white solid and purified by HPLC: A 1" column packed with 5 m C-18 functionalized silica (YMC Corp.) was flushed with 90% CH$_3$CN in 0.2% HOAc (B) water followed by equilibration with 300 ml of 0.2% HOAc (A) at 12 ml/min flow rate. The crude sulfone was dissolved in 10 ml of HOAC and diluted with 150 ml of water before being loaded onto the column and followed by 100 ml of A. A gradient to 100% B was run over 60 min, and fractions which appeared clean by analytical HPLC were pooled and lyophilized. The yield was 350 mg (63%) of white solid, over 90% pure by analytical HPLC, mp 120°–125°. $^1$H NMR (400 mHz, CDCl$_3$, PPM) 4.9, dd (j=3.5, 9.1 Hz), 1H. 4.1, dd (j=5.3, 10 Hz), 2H. 3.7, s, 2H. 3.69–3.65, dd (j=3.6, 14.6 Hz), 1H. 3.6, t (j=6.4 Hz), 1H. 3.5–3.45, m, 3H. 2.8, (symmetrical 6 peak resonance with j=7 Hz), 8H. 2.3, m, 2H. 1.9, m, 2H. 0.9, t (j=7 Hz), 12 H. $^{13}$C NMR (100 mHz, CDCl$_3$, PPM): 177.05, 176.01, 173.00, 60.79, 56.60, 56.26, 50.05, 44.25, 42.04, 41.99, 33.82, 28.30, 16.07. M/e (Finnigan MALDI TOF) 575, (MH+) 596 (MNa+).

Anal. Calc'd for C$_{20}$H$_{40}$O$_{10}$N$_5$PS.2H$_2$O: C, 39.40. H, 7.27. N, 11.48. Found: C, 39.16. H, 7.36. N, 11.78.

EXAMPLE 2

Synthesis of Glutathione Coupled to a Phosphorodiamidate Mustard: γ-Glutamyl-α-Aminopropionyl (β-(2-ethyl-N,N,N,N-tetra( 2'-chloro)ethylphosphoroamidate)sulfonyl)glycine (TER 231)

TER 231 is of the formula

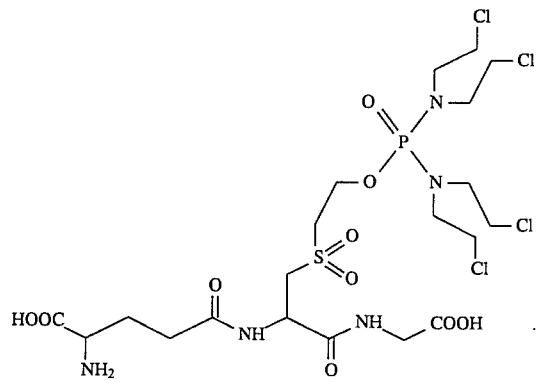

This is an analogous compound to TER 230 which contains a phosphoramidite mustard to produce the product:

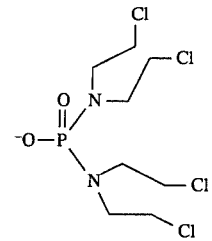

when activated by GST.

TER 231 was synthesized according to Reaction Scheme 2, set forth above.

2-bromoethyl N,N,N,N, -tetra(2'-chloroethyl)phosphoramidite, 6b 14 ml (100 mM) of triethylamine were slowly added over 5 min to a stirred solution of 9.3 ml (100 mM) of phosphorus oxychloride in 450 ml of CH$_2$Cl$_2$ chilled to 0° under argon, in a 1000 ml 3-necked flask fitted with a mechanical stirrer. Next, a solution of 7.09 ml (100 mM) of 2-bromoethanol in 50 ml CH$_2$Cl$_2$ was added slowly over 4 hrs. The mixture was stirred overnight and allowed to warm to rt. The solution was rechilled to 0°, and 35.7 g (200 mM) of bis-(2-chloroethyl)amine hydrochloride was added as a solid. To this stirred suspension was added a solution of 61.33 ml (440 mM) triethylamine in 100 ml Ch$_2$Cl$_2$ dropwise over 3 hrs. The mixture was allowed to warm to rt and was stirred for 3 days. The suspension was suction filtered, and the filtrate reduced in vacuo to a brown, viscous oil. This was mixed with 100 ml EtOAc, and filtered again to remove triethylamine hydrochloride. The solution was concentrated to about 50 ml in volume, and subjected to chromatographic purification. A bed of silica 38 by 5.5 cm was used, eluted with EtOAc:Pet. Ether 1:1. 12.3 g (27% yield) of clear yellow oil was isolated, r.f. 0.5. M/e (Finnigan MALDI TOF) 454.2, (MH+). $^1$H NMR (300 mHz, CDCl$_3$), PPM: 4.4–4.3, m, 2H. 3.75–36, t, j=2.2 Hz, 8H. 3.6–3.5, t, j=5Hz, 2H. 3.5–3.4, m, 8H.

γ-glutamyl-α-aminoβ-(2-ethyl-N,N,N,N,tetra(2-chloroethyl)-phosphoramidate)sulfidylpropionyl-glycine, 2b 4.5 g (15 mM) of glutathione was dissolved in 75 ml of deionized water and the pH was adjusted to 9–10 by adding 1N NaOH. To this stirred solution at rt was added a solution of 13 in 100 ml of ethanol. The turbid mixture became clear after two min, and was stirred overnight. TLC monitoring showed partial reaction, and the mixture was stirred another 3 days. The solution was then neutralized with to pH5–6, and the ethanol was removed in vacuo. The solution was divided into three roughly equal portions, and purified by prep HPLC as for 2a to give 0.5 g (36% yield) of white powder, mp 80° (dec.). M/e (Finnigan MALDI TOP) 680.2 (MH+). $^1$H NMR (300 mHz, DMSO D$_6$, PPM: 8.8–8.7 t, j=1.5 Hz, 1H. 8.5–8.4, d, j=2.5 Hz, 1H. 4.5–4.4, broad s, 1H. 4.1–4,0, dd, j=2.2, 1.8 Hz, 2H. 3.8–3.6, m, 10 H. 3.5–3.2, broad m, 12 H. 3.0–2.9, dd, j=1.3, 3.2 Hz, 1H. 2.9–2.8, t, j=1.9 Hz, 1H. 2.75–2.65, dd, j=3.2, 1.3 Hz, 1H. 2.4–2.3, m, 2H. 2.0–1.85, m, 2H.

Anal. Calc'd for C$_{20}$H$_{36}$N$_5$O$_8$PSCl$_4$·3H$_2$O: C, 32.75. H, 5.77. N, 9.54. Found: C, 33.05; H, 5.38. N, 9.42.

γ-glutamyl-α-Amino-β-(2-ethyl-N,N,N,N-tetra(2'-chloro)ethylphosphoroamidate)sulfonylpropionylglycine, 1b, TER 231

1.5 g (2.2 mM) of 2b was dissolved in 22 ml of HOAc, and 0.78 ml (4 mM) of 30% H$_2$O$_2$ was added. After 2 hrs, a mass spectrum of the mixture revealed complete conversion to the sulfoxide. 0.525 ml (2.5 mM) of 32% peracetic acid was added, and the reaction was stirred overnight. A mass spectrum of the mixture revealed almost total conversion of the material to the desired compound, and the mixture was lyophilized and purified by HPLC with the same method as for TER 230 to give 1.05 g (67% yield) of TER 231 as a white powder, mp 95° (dec.) .M/e (Finnigan MALDI TOF) 712.7 (MH+). $^1$H NMR, 300 mHz, D$_2$O, PPM: 5.2–5.1 m, 1H. 4.6–4.6, d, j=1.4 Hz, 2H. 4.0, s, 2H. 3.95–3.9, m, 1H. 3.85–3.65, m, 12H. 3.55–3.45, m, 8H. 2.2–2.5, m, 2H. 2.3–2.15, m, 2H.

Anal. Calc'd for C$_{20}$H$_{36}$N$_5$O$_{10}$PSCl$_4$·2H$_2$O: C, 32.14. H, 5.41. N, 9.37. Found: C, 32.07. H, 5.11. N, 9.22.

Additional Glutathione Analog Prodrugs

In a manner completely analogous to that set forth for the preparation of TER231 set forth above, the following additional analogs were prepared:

γ-glutamyl-α-Amino-β-((2-ethyl-N,N,N,N-tetra(2'-chloro) ethylphosphoroamidate)sulfonyl)propionyl-(R)-(–)-phenylglycine (TER 286);

γ-glutamyl-α-Amino-β-((2-ethyl-N,N,N,N-tetra(2'-chloro)ethylphosphoroamidate)sulfonyl)propionylphenylalanine (TER 303);

γ-glutamyl-α-Amino-β-(1-phenyl, (2'ethyl-N,N,N,N-tetra( 2'-chloro)ethylphosphoroamidate)sulfonyl) propionyl glycine (TER 296);

γ-Glutamyl-α-Amino-β-(1-phenyl, (2-ethyl N,N,N,N-tetra( 2'-chloro)ethylphosphoroamidate)sulfonyl) propionyl (R)-(–)-phenylglycine (TER 297).

Further details with respect to TER 286 may be found in Lyttle, M. H. et al. *J Med Chem* (1994) 37:1501–1507; Lyttle, M. et al. *J Med Chem* (1994) 34:189–194.

EXAMPLE 3

Selective Release of "L" by GST Isoenzymes

The compound to be tested was dissolved in 0.2M phosphate buffer and a solution of GST was added. The final concentration was 0.3 mM test compound and 0.006 mM GST, pH 7.3 for TER 230; for TER 231 GST was 0,003 mM, pH 7.1. The solution was incubated at 37°. Decomposition was followed by HPLC. The column was J. T. Baker C$_{18}$ 250×4.6 mm with 5μ particles. The A buffer was 0.05M ammonium acetate, pH 5.5; 5% CH$_3$CN; B buffer was 70% CH$_3$CN in A.

The column was run with a gradient of 20%–50% B over 15 min. then to 100% B in 3 mins; then back to 20% B over 6 mins. A 10 μL sample was injected and the flow rate was 1 ml/min. Aliquots were removed and catalytic decomposition was quenched by addition of acetic acid. Overnight HPLC utilizing an autosampler were used; the rates of decomposition were calculated by measuring the rate of disappearance of the peak versus an internal standard which was 0.06 mM of an inert peptide marker. The results for TER230 are shown in FIG. 1 and those for TER 231 are shown in FIG. 2.

As shown in FIG. 1, M1a decomposes TER 230 about 4 times faster than background and P1 decomposes TER 230 about 2 times faster than background. Both of these isoenzymes are predominantly expressed in many tumors. The isoenzyme A1, usually associated with healthy tissues, does not accelerate the decomposition of TER 230 above background within experimental error.

Figure 2:
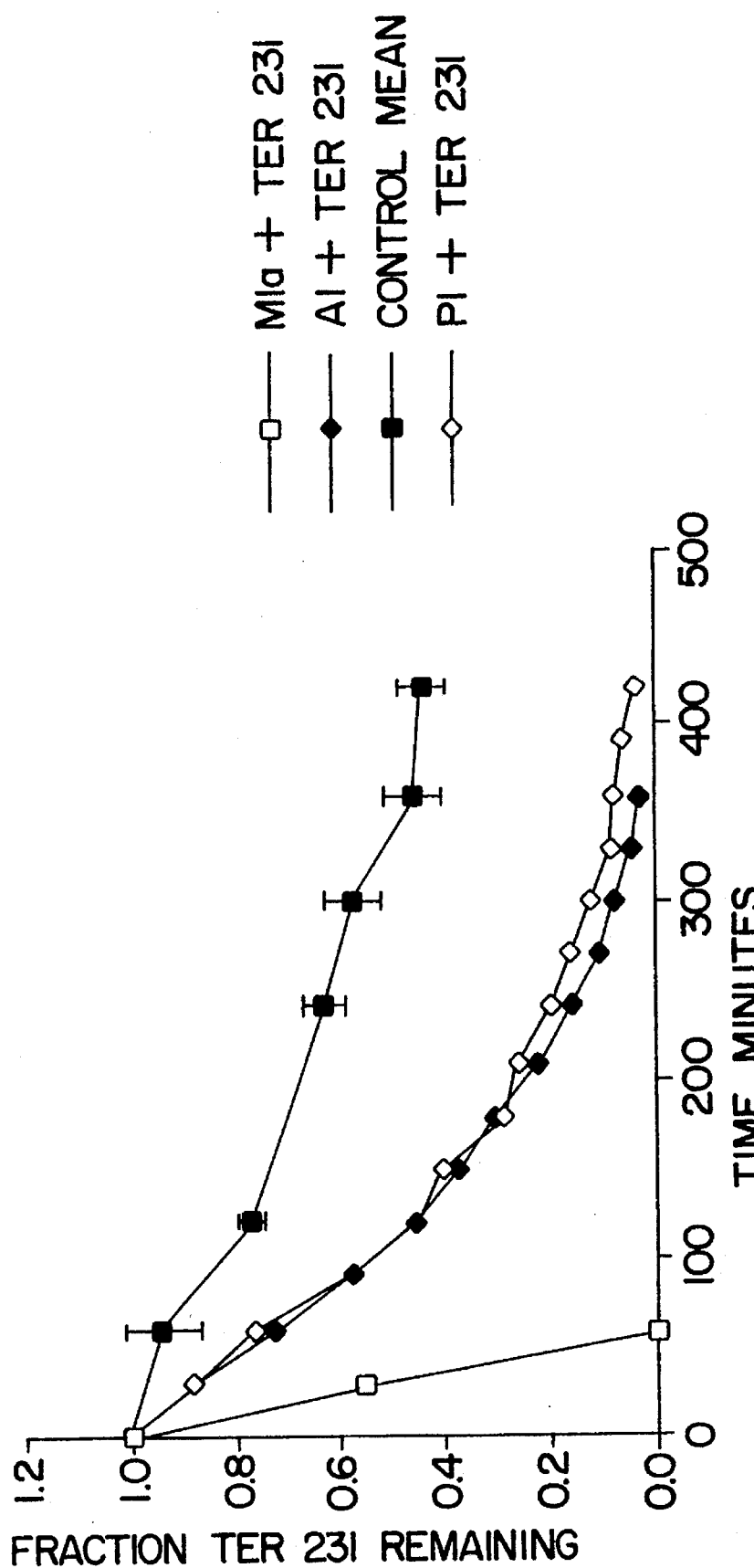
FIG. 2 is a graph showing the decomposition of TER 231 by various GSTs.

Similarly, as shown in FIG. 2, M1a decomposes TER 231 about 12 times faster than background; and P1 and A1 decompose TER 231 5 times faster than background. TER 231 in general decomposes more quickly than TER 230, probably due to the electron withdrawing effect of the four chlorines.

Figure 3:
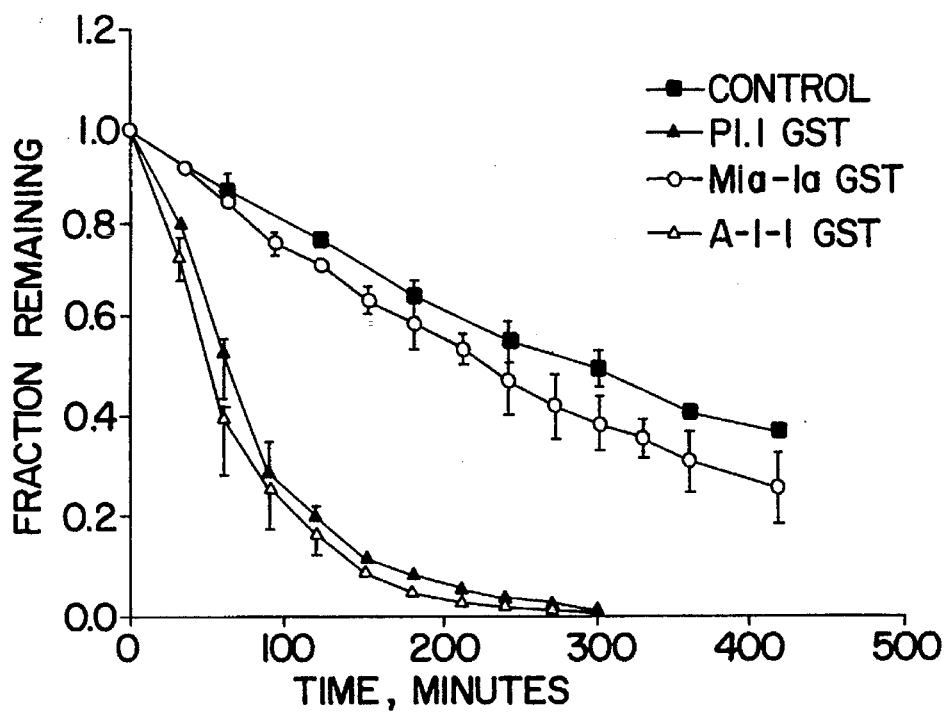
FIG. 3 is a graph showing the decomposition of TER 286 by various GSTs.

TER 286 was similarly tested with the results shown in FIG. 3. Both P1-1 and A1-1 accelerate the cleavage of TER 286 roughly six times faster than background; there is negligible acceleration of cleavage with M1a-1a.

In addition, half-lives were determined as described above using 3 μM recombinant human GST P1-1, A1-1 or M1a-1a starting with a concentration of the compound to be tested at 300 μM and monitoring disappearance using HPLC. Table 1 below shows the results:

TABLE 1

| IN VITRO HALF LIVES (min.) | | | | |
| --- | --- | --- | --- | --- |
| Compound: | 296 | 286 | 303 | 231 |
| Selectivity: | P1-1 | P1-1/A1-1 | A1-1 | M1a-1a |
| CONTROL | 280 | 275 | 335 | 350 |

TABLE 1-continued

| IN VITRO HALF LIVES (min.) | | | | |
|---|---|---|---|---|
| P1-1 | 2.5 | 50 | 310 | 110 |
| A1-1 | 200 | 65 | 45 | 110 |
| M1a-1a | 50 | 225 | 200 | 25 |

As seen in the table, depending on the prodrug selected, specificity can be obtained for any of the three human GSTs tested. Thus, TER 296 is selectively cleaved by P1-1; TER 286 is selectively cleaved by P1-1 and A1-1; TER 303 is selectively cleaved by A1-1; and TER 231 by M1a-1a.

For these prodrugs, the decomposition will result in a cytotoxic effect due to the liberation of the phosphorodiamidate mustard. This is similar to the biologically active species responsible for action of cyclophosphamide, a widely used chemotherapy drug as activated by cytochrome P450 or mixed function oxidases. Activity results from attack of the N on the C—Cl bond leading to formation of a positively charged aziridine ring,

stabilized as a zwitterion with the free phosphate. The aziridinium species reacts as an alkylating agent with nucleophilic moieties on DNA and results in crosslinking when multiple alkylation occurs. Such crosslinking permanently disables the reproductive mechanism of the cells.

EXAMPLE 4

Screening for In Vitro Cytotoxicity

Those compounds which demonstrate release of phosphoramide type mustard moieties when reacted with GST can then be screened for in vitro cytotoxicity according to methods known in the art (see, for example, Borch II). Preliminary results using HT29 human cancer cells show that TER 231 is toxic to these cells, while TER 230 is not. This is the expected result as the moiety released from TER 230 is nontoxic.

Results with MCF-7 cancer cells and a corresponding π-transfect containing elevated levels of P1 GST also show the desired results. The π-transfected MCF-7 cells are more sensitive to TER 231 than are the untransfected cells.

The prodrugs described above were tested with various MCF-7 cells transfected either with a vector for generation of additional levels of GST P1-1 or a vector containing only the selection marker. P1-1 transfection resulted in a 13-fold elevation of this enzyme. These cells were obtained from Dr. Alan Townsend, Bowman Grace School of Medicine. Also tested were MCF-7 cells selected for cyclophosphamide resistance (MCF-CTX) and its wild-type counterpart. Cyclophosphamide resistance has been associated with elevated levels of aldehyde dehydrogenase; however, MCF-CTX also has a 3-fold elevation of GST activity compared to wild type. These cells were obtained from Dr. Beverly Teicher, Dana Farber Cancer Institute.

The assays were conducted by treating a suspension of $2 \times 10^5$ cells/ml for two hours with varying concentrations of the prodrug. The cells were then plated at 1,000–2,000 per well in 96-well plates and assayed on day 5 by a modified methylene blue assay described by Oliver, M. H. et al. *J Cell Science* (1989) 92:513–518.

Figure 4A:
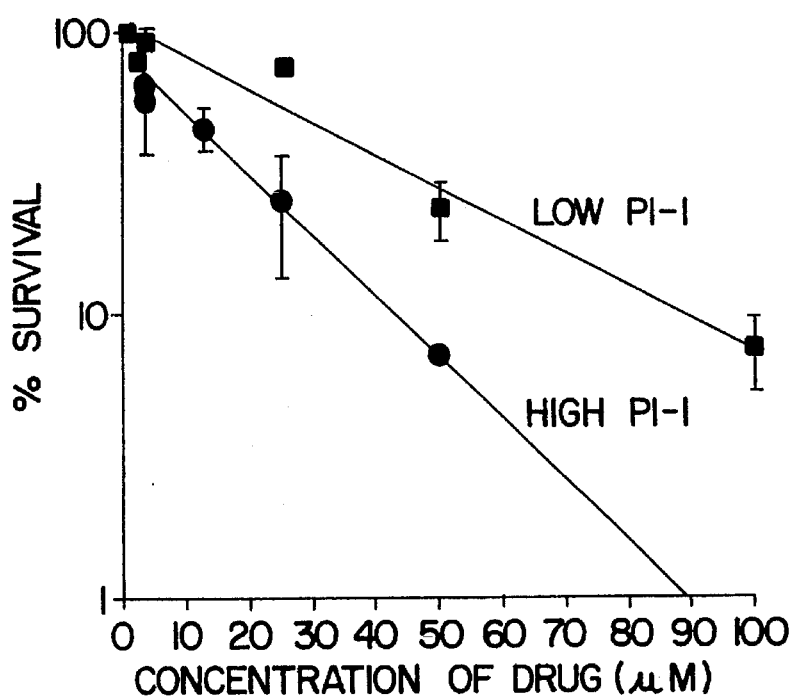
FIGS. 4a, 4b and 4c are graphs which show differential in vitro toxicity for various chemotherapeutic agents with respect to cells having high or low levels of GST P1-1.
Figure 4B:
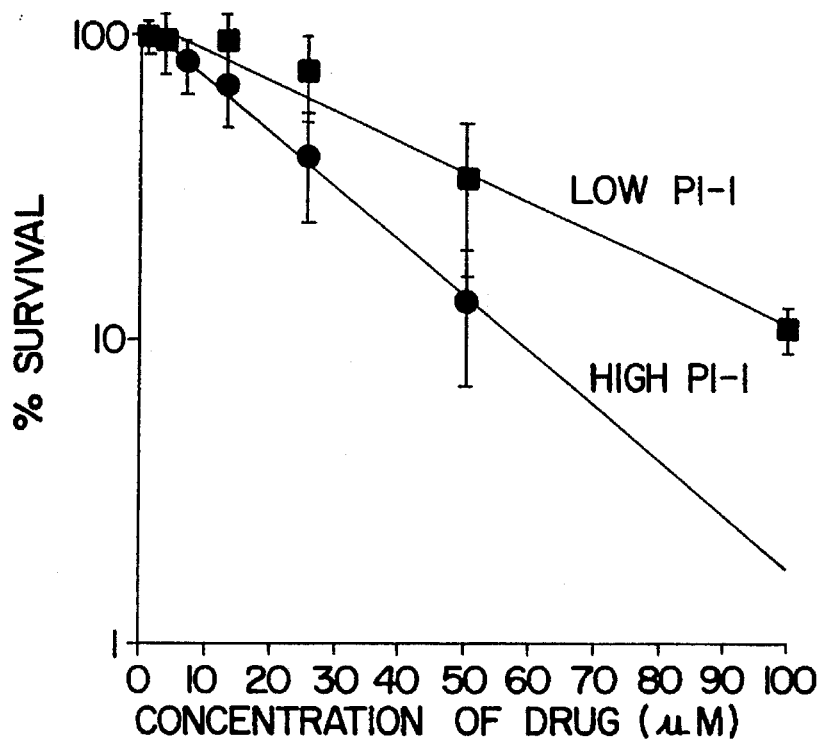
Figure 4C:
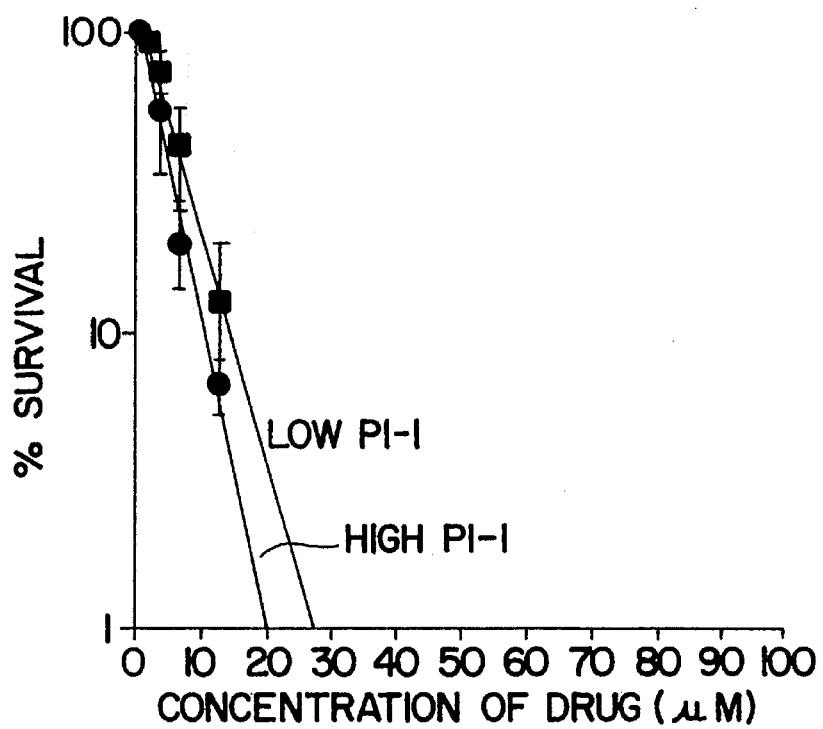

FIGS. 4a, 4b and 4c show the results obtained when MCF-7 tumor cells transfected by P1-1 were compared to cells transfected only with the control vector. As shown in FIG. 4a, when TER 286 is employed, cells containing high P1-1 enzyme levels are sensitized 4-fold to the prodrug compared to controls; FIG. 4b shows a 2-fold sensitization with respect to TER 231. When a standard toxic agent, such as mafosfamide is used, as shown in FIG. 4c, it makes no difference whether the cells have elevated or nonelevated GST P1-1 concentrations.

Similar results were obtained for MCF-7 cells which are sensitive to CTX as compared to CTX-resistant forms. The CTX-resistant cells were more sensitive to TER 286 by a factor of 1.8 as compared to cells sensitive to CTX in a standard clonogenic assay.

EXAMPLE 5

In vivo Cytotoxicity

Figure 5:
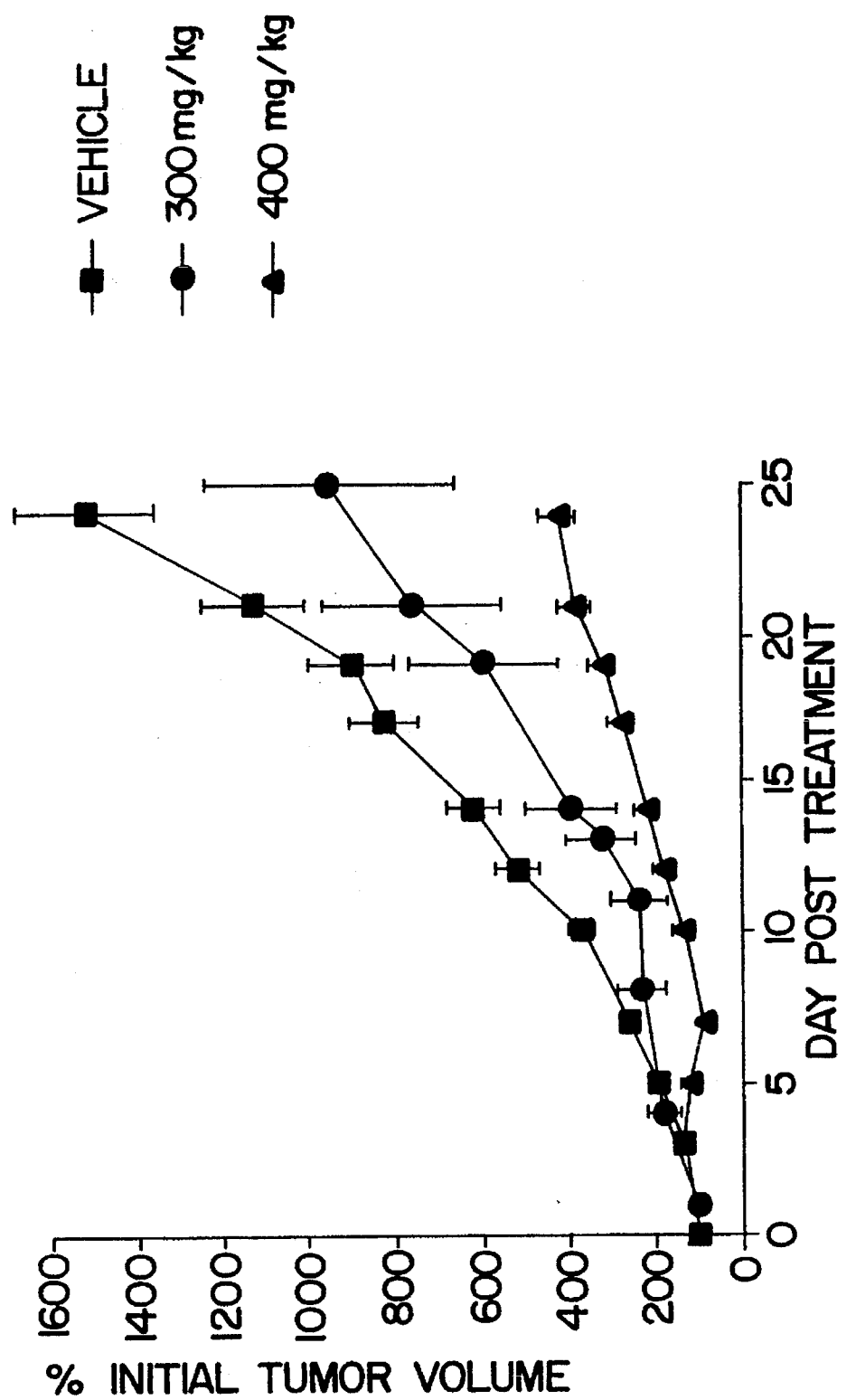
FIG. 5 shows the effect of TER 286 on growth of tumors in mice.

The prodrugs of the invention were tested in Balb/C nu/nv mice. The mice were implanted subcutaneously with MX-1 tumor pieces and then treated with a single intraperitoneal injection once tumors reached an average of 100 mm³ (which is at approximately day 18 post-implant). Tumor growth and body weight were monitored for one month following treatment. The results are shown in FIG. 5. As shown, the tumor volume in the treated mice as compared to controls is greatly diminished. In FIG. 5, the squares represent controls; circles represent 300 mg/kg of TER 286; triangles represent 400 mg/kg of the same drug. The points shown are the mean ±SEM of 5–7 mice per group.

EXAMPLE 6

Effect of Prodrug on Bone Marrow

Figure 6:
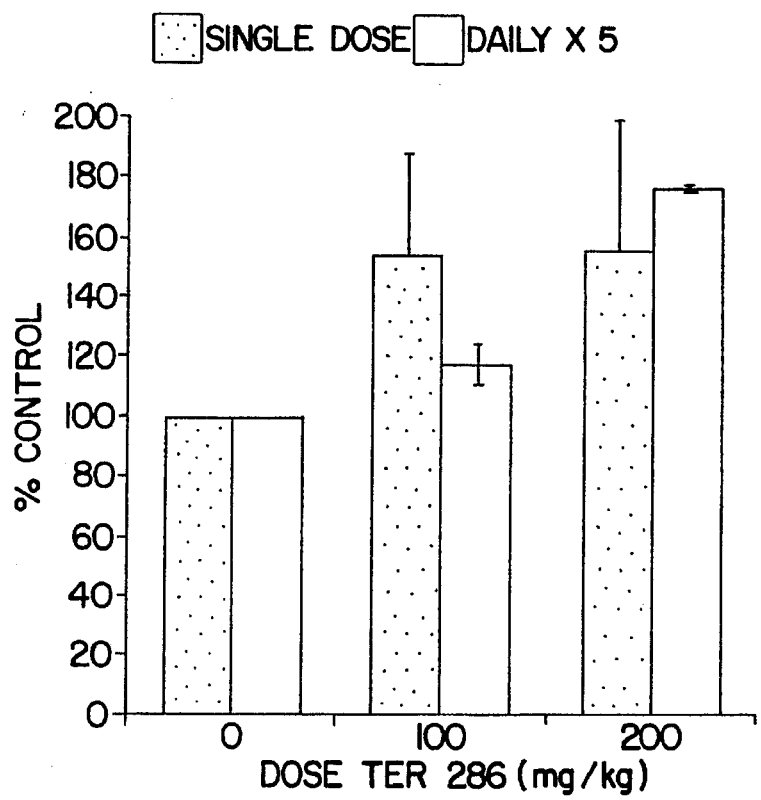
FIG. 6 shows the effect of 100–200 mg/kg TER 286 on the GM-CFU in bone marrow of mice.

In the assay, $B6D2F_1$ mice were treated with various doses of TER 286 intraperitoneally either as a single injection or as five daily injections. Femoral bone marrows were harvested 24 hours later and assayed for GM-CFU by the method of East, C. J. et al. *Cancer Chemother Pharmacol* (1992) 31:123–126. The results are shown in FIG. 6. Increases up to 180% of controls for GM-CFU were obtained with administration of 100–200 mg/kg of TER 286; the values shown are the mean plus SD of 2–3 experiments.

Figure 7:
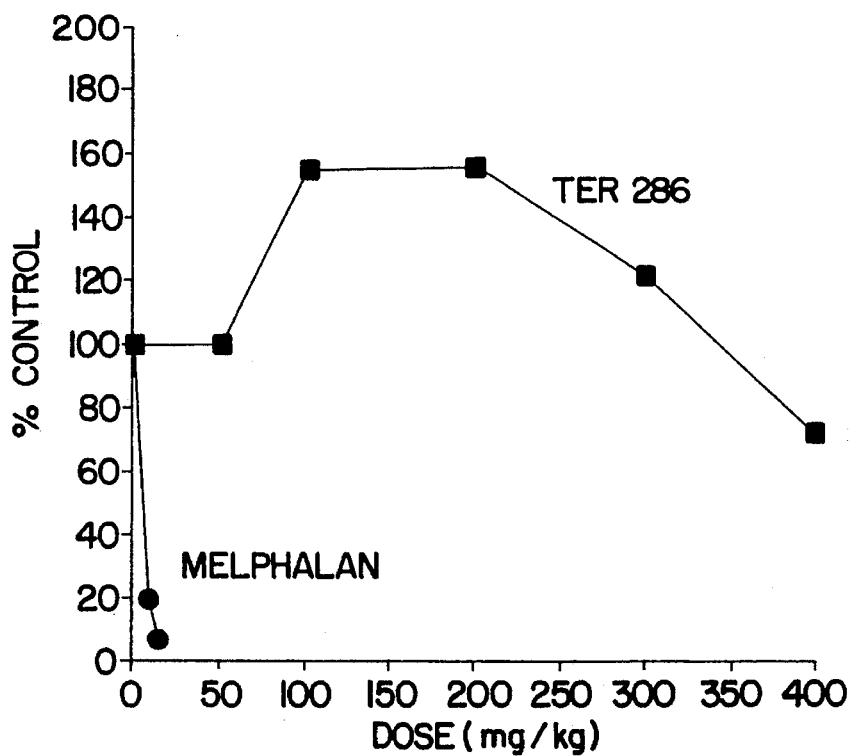
FIG. 7 shows the dose-dependence of bone marrow GM-CFU for administration of TER 286.

Further, as shown in FIG. 7, the optimum dosage range appears to be in this region of 100–200 mg/kg for TER 286. This result is especially remarkable since the prodrug is capable of generating cytotoxicity per se; the results with melphalan shown in the figure indicate extreme toxicity for chemotherapeutic agents with respect to bone marrow.

We claim:

1. A compound of the formula:

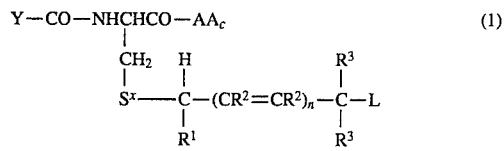

or the amides, esters or salts thereof, wherein:

L is an electron withdrawing leaving group;

$S^x$ is S=O, O=S=O, S=NH, HN=S=O, Se=O, O=Se=O, Se=NH, HN=Se=O, $S^+R^4$ wherein $R^4$ is alkyl (1–6C), or O—C=O or HN—C=O;

each R of $R^1$, $R^2$ and $R^3$ is independently H or a noninterfering substituent;

n is 0, 1 or 2;

Y is selected from the group consisting of

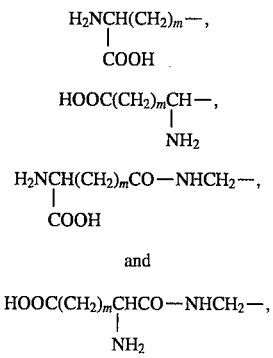

wherein m is 1 or 2; and $AA_C$ is alanine, β-alanine, phenylalanine, glycine or phenylglycine linked through a peptide bond to the remainder of said compound of formula 1.

2. The compound of claim 1 wherein L is a biologically active moiety when released from the compound of formula 1.

3. The compound of claim 2 wherein said biologically active moiety is a phosphoramide mustard or a phosphorodiamidate mustard.

4. The compound of claim 1 wherein n=0.

5. The compound of claim 1 wherein Y—CO is γ-glutamic acid.

6. The compound of claim 1 wherein each $R^3$ is independently H, lower alkyl (1–4C) or phenyl.

7. The compound of claim 1 wherein n=0; $R^1$ and each $R^3$ are independently H or phenyl, Y—CO is γ-glu and $AA_C$ is glycine, phenylglycine, β-alanine, alanine or phenylalanine.

8. The compound of claim 7 wherein L is —OP(O)(N(CH$_2$CH$_3$)$_2$)$_2$, —OP(O)(N(CH$_2$CH$_2$Cl)$_2$)$_2$, —OP(O)(NHCH$_2$CH$_2$Cl)$_2$, —OP(O)(N(CH$_2$CH$_2$Br)$_2$)$_2$, —OP(O)(NHCH$_2$CH$_2$Br)$_2$, or 4-methoxy-2,3-di-t-butylphenoxy-.

9. The compound of claim 1 wherein $S^x$ is O=S=O.

10. The compound of claim 1 which has a formula selected from the group consisting of:

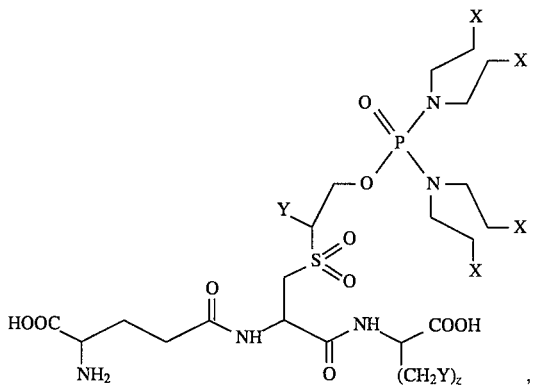

wherein each Y is independently H or phenyl; Z is 0 or 1; and X is H, Cl or Br including the amides, esters or salts thereof;

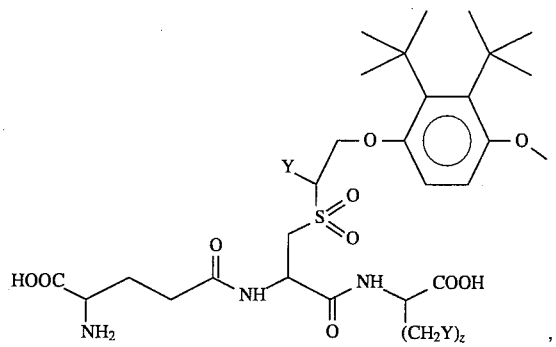

wherein each Y is independently H or phenyl; Z is 0 or 1; and X is H, Cl or Br including the amides, esters or salts thereof; and

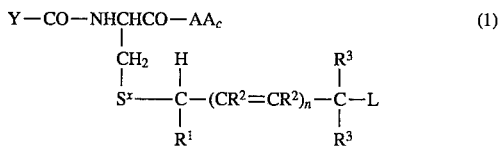

wherein each Y is independently H or phenyl; Z is 0 or 1; and X is H, Cl or Br including the amides, esters or salts thereof.

11. A pharmaceutical composition effective in treating MCF-7 cells, which composition comprises at least one compound of of the formula:

$$Y-CO-NHCHCO-AA_c \quad (1)$$
$$\begin{array}{c} | \\ CH_2 \quad H \quad R^3 \\ | \quad | \quad | \\ S^x\text{———}C-(CR^2=CR^2)_n-C-L \\ | \quad \quad \quad \quad \quad | \\ R^1 \quad \quad \quad \quad R^3 \end{array}$$

or the amides, esters or salts thereof, wherein:

L is an electron withdrawing leaving group;

$S^x$ is S=O, O=S=O, S=NH, HN=S=O, Se=O, O=Se=O, Se=NH, HN=Se=O, $S^+R^4$ wherein $R^4$ is alkyl (1–6C), or O—C=O or HN—C=O;

each R Of $R^1$, $R^2$ and $R^3$ is independently H or a noninterfering substituent;

n is 0, 1 or 2;

Y is selected from the group consisting of

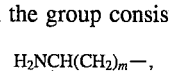

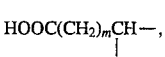

-continued $$HOOC(CH_2)_m\underset{\underset{NH_2}{|}}{C}HCO-NHCH_2-,$$

wherein m is 1 or 2; and

AA$_C$ is an amino acid selected from the group consisting of: glycine, valine, alanine, β-alanine, 4-amino butyric acid, aspartic acid, phenylglycine, histidine, tryptophan, tyrosine, unsubstituted phenylalanine, and phenylalanine substituted in its aromatic ring by one or two substituents selected from the group consisting of halo, OR, SR, and NR$_2$, wherein R is H or alkyl (1–4C), linked through a peptide bond to the remainder of said compound of formula 1 in admixture with a pharmaceutically acceptable excipient.

12. A compound of claim 1 which is selected from the group consisting of

γ-glutamyl-α-Amino-β-((2-ethyl-N,N,N,N-tetra(2'-chloro)ethylphosphoroamidate)sulfonyl)propionylglycine, (TER 231);

γ-Glutamyl-α-Amino-β-((2-ethyl-N,N,N,N-tetra(2'-chloro)ethylphosphoroamidate)sulfonyl)propionyl-(R)-(–)-phenylglycine (TER 286);

γ-Glutamyl-α-Amino-β-((2-ethyl-N,N,N,N-tetra(2'-chloro)ethylphosphoroamidate)sulfonyl)propionylphenylalanine (TER 303);

γ-Glutamyl-α-Amino-β-(1-phenyl, 2-ethyl-N,N,N,N-tetra(2'-chloro)ethylphosphoroamidate)sulfonyl)propionyl glycine (TER 296);

γ-Glutamyl-α-Amino-β-(1-phenyl, 2-ethyl-N,N,N,N-tetra(2'-chloro)ethylphosphoroamidate)sulfonyl)propionyl (R)-(–)-phenylglycine (TER 297);

including the amides, esters or salts thereof.

13. The compound of claim 12 which is γ-Glutamyl-α-Amino-β-((2-ethyl-N,N,N,N-tetra(2'-chloro)ethylphosphoroamidate)sulfonyl)propionylglycine, (TER 231), including the amides, esters or salts thereof.

14. The compound of claim 12 which is γ-Glutamyl-α-Amino-β-((2-ethyl-N,N,N,N-tetra(2'-chloro) ethylphosphoroamidate)sulfonyl)propionyl-(R)-(–)phenylglycine (TER 286), including the amides, esters or salts thereof.

15. The compound of claim 12 which is γ-Glutamyl-α-Amino-β-((2-ethyl-N,N,N,N-tetra(2' -chloro)ethylphosphoroamidate)sulfonyl)propionylphenylalanine (TER 303), including the amides, esters or salts thereof.

16. The compound of claim 12 which is γ-Glutamyl-α-Amino-β-(1-phenyl, 2-ethyl-N,N,N,N-tetra(2'-chloro)ethylphosphoroamidate)sulfonyl)propionyl glycine (TER 296), including the amides, esters or salts thereof.

17. The compound of claim 12 which is γ-Glutamyl-α-Amino-β-(1-phenyl, 2-ethyl-N,N,N,N-tetra(2'-chloro)ethylphosphoroamidate)sulfonyl)propionyl (R)-(–)-phenylglycine (TER 297), including the amides, esters or salts thereof.

* * * * *

UNITED STATES PATENT AND TRADEMARK OFFICE
CERTIFICATE OF CORRECTION

PATENT NO. : 5,556,942
DATED : September 17, 1996
INVENTOR(S) : Kauvar et al.

It is certified that error appears in the above-identified patent and that said Letters Patent is hereby corrected as shown below:

<u>Column 21,</u>
Lines 50-65, part of formula reading "$(CH_2Y)_z$" should read -- $(CH_2)_zY$ --;

<u>Column 22,</u>
Lines 5-15, part of formula reading "$(CH_2Y)_z$" should read -- $(CH_2)_zY$ --;

Lines 20-30, part of formula reading "$(CH_2Y)_z$" should read -- $(CH_2)_zY$ --.

Signed and Sealed this

Twenty-sixth Day of August, 2003

JAMES E. ROGAN
*Director of the United States Patent and Trademark Office*